US00PP10742P

United States Patent [19]

Bautista

[11] Patent Number: Plant 10,742

[45] Date of Patent: Dec. 29, 1998

[54] HELICHRYSUM PLANT NAMED 'HARVEST PLUM'

[75] Inventor: Rodolfo Valdoz Bautista, Half Moon Bay, Calif.

[73] Assignee: Bay City Flower Company, Inc., Half Moon Bay, Calif.

[21] Appl. No.: 841,412

[22] Filed: Apr. 22, 1997

[51] Int. Cl.[6] ..... A01H 5/00

[52] U.S. Cl. ..... Plt./68.1

[58] Field of Search ..... Plt./68.1

[56] References Cited

U.S. PATENT DOCUMENTS

| | | | |
|---|---|---|---|
| P.P. 9,660 | 10/1996 | Bautista | Plt./68.1 |
| P.P. 9,661 | 10/1996 | Bautista | Plt./68.1 |
| P.P. 9,666 | 10/1996 | Bautista | Plt./68.1 |
| P.P. 9,667 | 10/1996 | Bautista | Plt./68.1 |
| P.P. 10,193 | 1/1998 | Elliot et al. | Plt./68.1 |

*Primary Examiner*—Howard J. Locker
*Assistant Examiner*—Kent L. Bell
*Attorney, Agent, or Firm*—James R. Cypher; Charles R. Cypher

[57] ABSTRACT

The present invention relates to a new and distinct variety of the Compositae family, named *Helichrysum bracteatum* 'Harvest Plum', which originated as a seedling from the inventor's controlled crossing of *Helichrysum bracteatum* (Venten.) Andr. 'Harvest Pink Picotte' with a dark pink variety of *Helichrysum bracteatum* (Venten.) Andr. The new variety is distinguished from *Helichrysum bracteatum* (Venten.) Andr. 'Harvest Pink Picotee' and all other varieties kown to the inventor by the color of its flower and buds, its resistance to the root disease Pythium, its puberulent and sparsely villous leaves, its compact growth habit, its ability to grow well in pots, and the ease with which it can be forced to flower outside for sale in the autumn without growth regulators. The new variety further possesses the commercially and aesthetically desirable characteristic of having long-lasting flowers.

3 Drawing Sheets

BACKGROUND OF THE INVENTION

The present invention relates to a new and distinct variety of the Compositae family. The new variety was named *Helichrysum bracteatum* 'Harvest Plum' by the assignee, Bay City Flower Company, Inc. The inventor is Rodolfo Valdoz Bautista of Half Moon Bay, Calif., a citizen of the Philippines.

This new Helichrysum variety originated as a seedling, It was selected from the f3 generation of a series of controlled hybridizations conducted by the inventor in a commercial nursery in the city of Half Moon Bay. Half Moon Bay is located in San Mateo County, in the state of California.

The inventor first crossed *Helichrysum splendidum* (Thunb.) Less. and *Helichrysum bracteatum* (Venten.) Andr. This cross produced the f1 generation. Fron the f1 generation the inventor selected an individual seedling known as '1A93'. The individual known as '1A93' was selected for further hybridization because of its unique flower head color and compact growth habit. The seedling '1A93' is also designated by the formula *Helichrysum splendidum* (Thunb.) Less.×*Helichrysum bracteatum* (Venten.) Andr.

'1A93' was crossed back to *Helichrysum bracteatun* (Venten.) Andr. From the progeny of this cross, the f2 generation, the inventor selected an individual seedling for commercial development and further hybridization. The individual was designated *Helichrysum bracteatum* (Venten.) Andr. 'Harvest Pink Picotee'.

'Harvest Pink Picotee' is readily characterized by the unique color pattern of its bracts which produces a mature flower head that is primarily white with a pink circumference. Most of the involucral bracts of 'Harvest Pink Picotee' are distinctly patterned. The exceptions are the innermost bracts which do not appear until the flower is fully mature. The innermost bracts are primarily white and have lighter tips than the earlier-appearing bracts. The outermost bracts are the most vibrantly colored. The tips of the outermost involucral bracts are a dark red-purple (R.H.S. 59A). The upper middle portion of these involucral bracts are a lighter red-purple (R.H.S. 63C). The lower middle and basal portions of these bracts are white (R.H.S. 155D). The variety known as 'Harvest Pink Picotee' is protected by U.S. Plant Pat. No. 9,661, granted Oct. 15, 1996.

In the third hybridization, the inventor crossed *Helichrysum bracteatum* (Venten.) Andr. 'Harvest Pink Picotee' to a dark pink variety of *Helichrysum bracteatum* (Venten.) Andr. to produce the new variety described herein. In this cross 'Harvest Pink Picotee' was the seed parent. *Helichrysum bracteatum* (Venten.) Andr. was the pollen parent.

The new variety is particularly suitable for commercial plant culture because of its long-lasting flowers and attractive coloring.

The characteristics of the new variety which in combination distinguish it from *Helichrysum bracteatum* (Venten.) Andr. 'Harvest Pink Picotee' and all other varieties known to the inventor are: the color of its flower head and bud, its resistance to the root disease Pythium, its puberulent and sparsely villous leaves, its compact growth habit, its ability to grow well in pots in which it can be sold, and the ease with which it can be forced to flower outside for sale in the autumn without growth regulators.

The coloring of the flower head of the new variety changes as the flower head opens revealing more bracts. The bud stage is darkest. The tips of the bracts of the buds are greyed-purple (R.H.S. 187A). The lower portion of the bracts are red-purple (R.H.S. 67B).

When the flower head is fully opened, the innermost bracts are revealed. The innermost bracts are almost completely white (R.H.S. 155C). The innermost bracts are much smaller than the middlebracts. The middle bracts are mostly red-purple (R.H.S. 66D) with a small base portion being white (R.H.S. 155C). Because only the innermost bracts are white and they are very small, the red-purple of the middle bracts dominates the color of the mature flower head. This is different from 'Harvest Pink Picotee' where the white basal portions of the inner and middle bracts dominate the tip color, and the flower head appears primarily white with a pink circumference.

When the flower head is only partially opened the tips of the middle bracts are most visible and the bracts of the inflorescence appear to be a uniform red-purple color (R.H.S. 66D).

The new variety, when planted in the summer for sale in the autumn season, can be forced to salable product in 11 to 13 weeks under prevailing daylengths and outdoor conditions in Half Moon Bay, Calif.

The following table compares the new vaariety to the closest varieties known to the inventor, according to the new variety's distinguishing characteristics:

| | *H. bracteatum* (general characteristics) | '1A93' | 'Harvest Pink Picotee' | 'Harvest Plum' |
|---|---|---|---|---|
| bract color | various colors | R.H.S. 4A | Bract tips: R.H.S. 59A. Bract base: R.H.S. 155D. (Base color dominates in inner and middle bracts.) | Bract tips: R.H.S. 66D. Bract base: R.H.S. 155C. (Tip color dominates in all but innermost bracts.) |
| bud color | various colors | R.H.S. 187B | R.H.S 59A | Bract tips: R.H.S. 187A. Bract base: R.H.S. 67B. |
| disease resistance | not resistant to Pythium | resistant to Pythium | resistant to Pythium | resistant to Pythium |
| leaf surface | puberulent | | | |
| suitability for pot culture | good | good | good | good |
| ease of forcing | generally good | good | good | good |
| growth habit | generally compact | compact | compact | compact |
| flowering habit | long-lasting | 7 weeks | 7 weeks | 7 weeks |

The distinguishing characteristics are retained by asexually reproduced, successive generations. The inventor, at a commercial nursery in Half Moon Bay, Calif., has asexually reproduced the new variety through three successive generations by means of cuttings and has found that the combination of characteristics as herein disclosed remain firmly fixed.

BRIEF DESCRIPTION OF THE DRAWINGS

The accompanying drawings consist of color photographs that show the typical potted-plant form, including the inflorescence, foliage, and bract color development from the bud stage to the mature flower head. The colors are represented as truly as possible using conventional photographic procedures.

DETAILED DESCRIPTION OF THE NEW VARIETY

Figure 1:
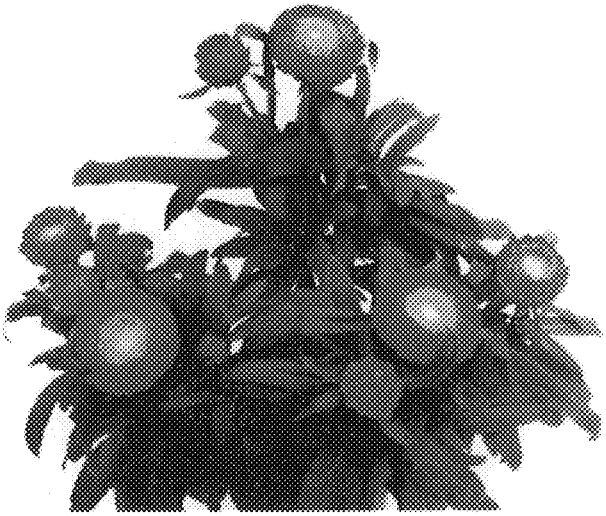
FIG. 1 is a perspective view of a potted plant of the new variety described herein, illustrating the overall form and appearance of the plant in full bloom.
Figure 2:
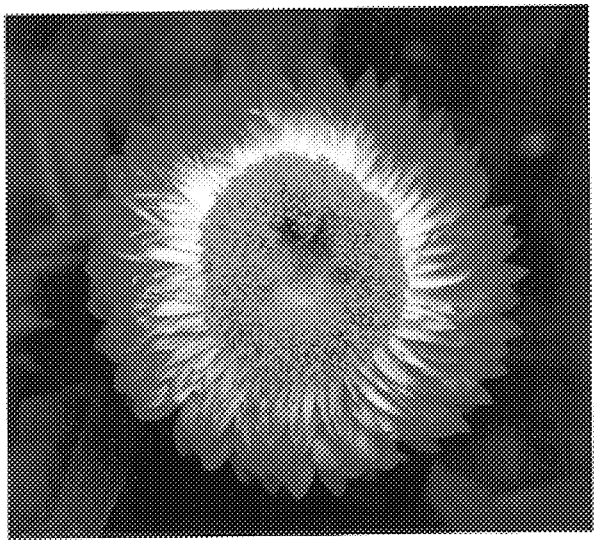
FIG. 2 is a top view of a mature flower head of the new variety described herein, showing the pigmentation pattern of the involucral bracts.
Figure 3:
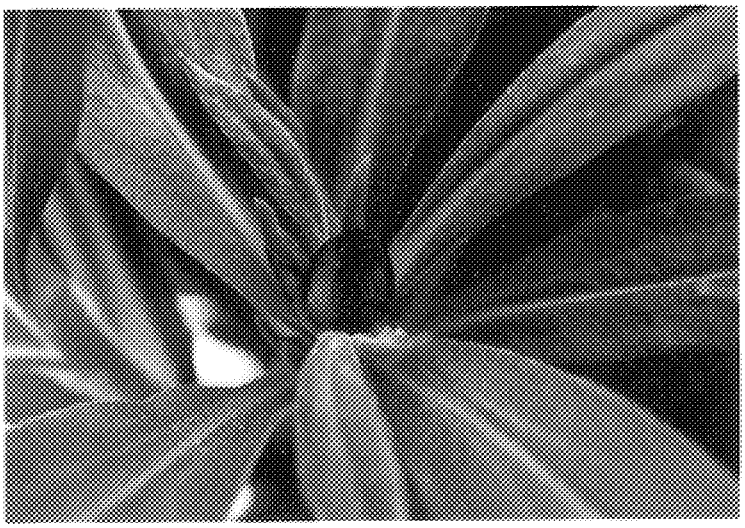
FIG. 3 is a view of a bud of the new variety described herein.
Figure 4:
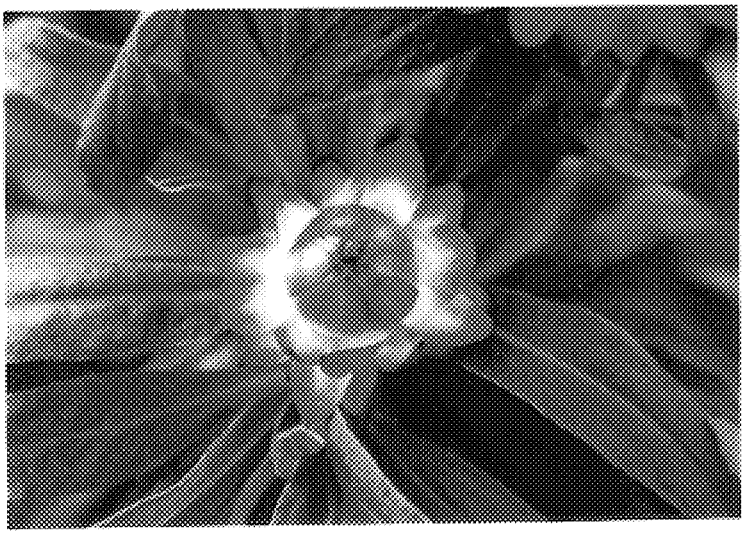
FIG. 4 is a view of a flower head which is beginning to open, showing the overall appearance of the flower head at this stage.
Figure 5:
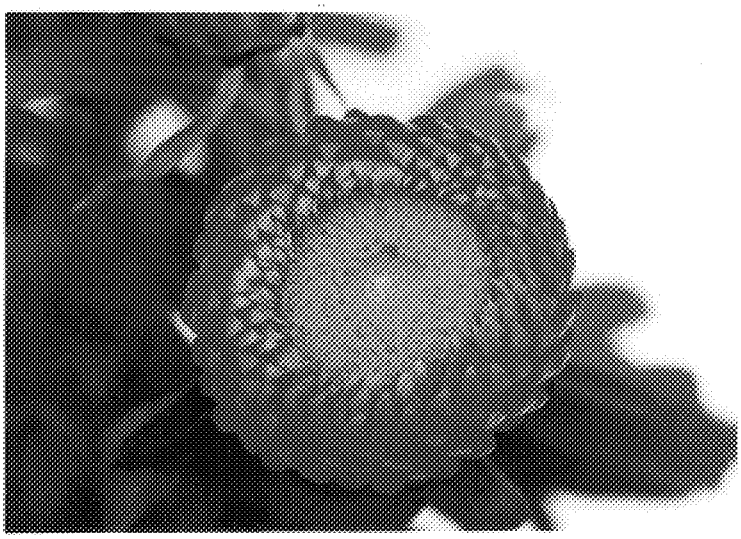
FIG. 5 is a view of a partially opened flower head.

The following is a detailed description of the new variety. The new variety has not been observed under all possible environmental conditions. Color designation and other values stated may deviate slightly from the stated values from flowering to flowering, but the deviations will be within the range expected from varying environmental, seasonal and cultural conditions. Color designations were made according to the R.H.S. Colour Chart published by The Royal Horticultural Society of London, England.

The following description is based on observations of optimally fertilized plants grown outside in 11 cm pots. Cuttings were taken from mature plants in the summer and placed in 4×5 cm cell trays. Roots began visible initiation after approximately 2 weeks. Plants were transplanted to 11 cm pots approximately 4 to 6 weeks after sticking, and moved out of the greenhouse. Plants were pinched 3 to 4 weeks after transplanting. The observed plants were 13 weeks old. The plants were grown under the prevailing daylengths and temperatures in Half Moon Bay, Calif., during the summer and autumn months. In Half Moon Bay, the average temperature during the day is 60 degrees Fahrenheit. The average temperature during the night is 51 degrees Fahrenheit.

The Plant

Name: *Helichrysum bracteatum* (Venten.) Andr. 'Harvest Plum'.

Origin: Seedling.

Parentage:

*Seed patent.*—*Helichrysum bracteatum* (Venten.) Andr. 'Harvest Pink Picottee'.

*Polen parent.*—*Helichrysum bracteatum* (Venten.) Andr.

Classification:

*Family.*—Compositae.

*Genus.*—Helichrysum.

*Species.*—*Helichrysum bracteatum* (Venten.) Andr. Bailey and Bailey and the staff of the Bailey Hortorium, *Hortus Third* (1976).

*Commercial.*—Strawflower.

Form: Upright, compact, biennial herb.

Height: Plant grown in 11 cm pot is 32 cm.

Circumference: Plant grown in 11 cm pot is 73 cm.

Growth: Upright, vigorous growth outdoors with excellent branching: easily forced to bloom without growth regulators.

Stems:

*Texture.*—Generally, stems are moderately pubescent; stems are very pubescent below the flower with fine cottony hairs that entirely cover the green stem and have a combed smooth appearance.

*Size.*—Stem width at top of plant is 5 mm. Stem width at base of plant is 5 mm. Stem width at widest point is 7 mm.

Foliage:

*Attachment.*—Semi-amplexicaul.

*Quantity.*—Abundant.

*Shape.*—Linear; narrowly acute; margins are repand.

*Size.*—As large as 14 cm long by 3.2 cm wide.

*Texture.*—Viscid; main vein dominates on the underside of leaf and is sunken on the leaf surface.

*Pubescence.*—Leaf surfaces are puberulent, and sparsely villous; main veins are hirsute.

*Color.*—Upper leaf surface is R.H.S. 137A (green group); lower leaf surface is R.H.S. 137B (green group).

*Petiole.*—Nonexistent.

Disease resistance: Resistance to the root disease Pythium.

The Bud

Form: Conical, with imbricate involucral bracts.

Teture: Smooth and glossy (waxy).

Rate of opening: Slowly, and in layers, closing at night; fully open in 2–3 weeks.

Size:

*Diameter.*—1.5 cm.

Involucral bracts:

*Color.*—Early pigmentation of bud is R.H.S. 187A (greyed-purple group) at tips of the bracts and R.H.S. 67B (red-purple group) in the middle portion of the bracts.

*Aspect.*—Thin, dry, membranous.

The Inflorescence

Form: Flower head is discoid and solitary; usualy 1 or 2 buds at the next leaf axis below.

Flower head size:

*Diameter.*—5.5–6.0 cm.

*Circumference.*—19 cm.

Disc floret portion diameter: 2.5–2.9 cm.

Shape of the flower head: Circular; involucral bracts are numerous and imbricate.

Appearance of the flower head: Showy.

Involucral bracts:

*Form.*—Involucral bracts are imbricate in many rows. Involucral bracts, are scarious and membranous, but are brightly colored. The involucral bracts are deltoid, enlarged and petal-like.

*Color.*—Outermost bracts are strongly two-toned. The tips of the outermost bracts are R.H.S. 74C (red-purple group) while the middle and base portions of these bracts are R.H.S. 155C (white group). These bracts are visible on the underside of a fully matured flower head. The middle bracts are also two-toned, with the colored tip portion dominating the white basal portion. The tips and middle portions of these bracts are R.H.S. 66D (red-purple group). The base portions of the middle bracts are also R.H.S. 155C. These bracts are visible on the upper side of the mature flower head. The small innermost bracts are mostly one color: R.H.S. 155C.

Disc florets:

*Form.*—Florets are all small, bisexual and tubular. The corolla of the florets is usually 5-lobed. Corolla is usually 11 mm long and glaucous (waxy). The upper 3.5 mm of the corolla is usually brightly colored.

*Androecium.*—There are usually 5 stamens borne on the corolla tube. The stamens, including the anthers, are usuallyunited into a tube around the style and become hightly reflexed from the point of separation. The stamens protrude from the corolla. Pollen occurs on the adaxial surface of the anthers.

*Gynoecium.*—One pistil per disc floret. The ovary is inferior. The style is often branched. The style protrudes from the corolla. The stigma is bright yellow.

*Color.*—The colored upper portion of the corolla is also bright yellow.

Pollen color: R.H.S. 23A (yellow-orange group).

Blooming habit: The new variety, when planted in the summer for sale in the autumn season, can be forced to salable product in 11 to 13 weeks under prevailing daylengths and outdoor conditions in Half Moon Bay, Calif. The terminal inflorescence persists approximately 7 weeks on the plant. Usually, lateral inflorescence are present and begin blooming as the terminal inflorescence dies. If old inflorescences are removed, new inflorescences will continue to appear and bloom. New buds are produced on new growth all year long, if growing conditions allow, such as under the prevailing daylengths and temperatures at Half Moon Bay, Calif.

Fragrance: none.

Achenes: Flowers produce nearly cylindrical or 5-angled achenes that are approximately 3 mm in length and 1 mm wide. The achenes have a pappus of bristles. The bristles can be either simple or plumose at their apex. The achenes are dry and hard. The achenes rarely germinate.

Suitability as cut flower: The new plant last 10 to 14 days as a cut flower. After 10 to 14 days, the flower head still substantially retains its shape and color, but the stems and foliage generally begin to rot.

I claim:

1. A new and distinct variety of Helichrysum plant, as illustrated and described.

* * * * *